US010346759B2

(12) United States Patent
Adams et al.

(10) Patent No.: US 10,346,759 B2
(45) Date of Patent: Jul. 9, 2019

(54) PROBABILISTIC INFERENCE ENGINE BASED ON SYNTHETIC EVENTS FROM MEASURED DATA

(71) Applicant: International Business Machines Corporation, Armonk, NY (US)

(72) Inventors: Samuel Scott Adams, Rutherfordton, NC (US); Robert R. Friedlander, Southbury, CT (US); James R. Kraemer, Santa Fe, NM (US); Kelly Grant Lee, Eden Prairie, MN (US)

(73) Assignee: International Business Machines Corporation, Armonk, NY (US)

( * ) Notice: Subject to any disclaimer, the term of this patent is extended or adjusted under 35 U.S.C. 154(b) by 811 days.

(21) Appl. No.: 14/867,103

(22) Filed: Sep. 28, 2015

(65) Prior Publication Data
US 2017/0091639 A1 Mar. 30, 2017

(51) Int. Cl.
*G06N 7/02* (2006.01)
*G06N 7/04* (2006.01)
*G06N 7/06* (2006.01)
*G06N 7/08* (2006.01)
*G06N 7/00* (2006.01)
*G06N 5/04* (2006.01)
*G16H 50/70* (2018.01)

(52) U.S. Cl.
CPC .......... *G06N 7/005* (2013.01); *G06N 5/046* (2013.01); *G16H 50/70* (2018.01)

(58) Field of Classification Search
CPC ......... G06N 7/005; G06N 5/046; G16H 50/70
See application file for complete search history.

(56) References Cited

U.S. PATENT DOCUMENTS

| 7,792,783 B2 | 9/2010 | Friedlander et al. |
| 8,055,603 B2 | 11/2011 | Angell et al. |
| 8,145,582 B2 | 3/2012 | Angell et al. |
| 8,204,869 B2 | 6/2012 | Paknad et al. |

(Continued)

FOREIGN PATENT DOCUMENTS

CN 103530309 1/2014

OTHER PUBLICATIONS

U.S. Appl. No. 14/721,091, filed May 26, 2015.

*Primary Examiner* — Scott A. Waldron
*Assistant Examiner* — Ababacar Seck
(74) *Attorney, Agent, or Firm* — Fleit Gibbons Gutman Bongini Bianco PL; Jon A. Gibbons

(57) ABSTRACT

Automatically create abstractions of large sets of data and then probabilistic inferences based on the abstractions. The probabilistic inference is derived from the logical hierarchy using Bayesian statistics to infer a probabilistic event based upon a characteristic of the data in a hierarchy of synthetic events. The logical hierarchy of a set of a plurality of synthetic events is related by at least one characteristic of data is built by accessing a first set of data. The first set of data is organized based on a first characteristic. A second set of data different than the first set of data is accessed. A second set of data based is organized based on a second characteristic. The first characteristic and the second characteristic are processed to generate a synthetic event. The synthetic event is a third set of data representing a result of a mathematical computation defined by an operation $S(p1) \Longrightarrow F(p2)$.

18 Claims, 4 Drawing Sheets

(56) References Cited

U.S. PATENT DOCUMENTS

| | | |
|---|---|---|
| 8,626,671 B2 | 1/2014 | Federgreen |
| 8,782,777 B2 | 7/2014 | Friedlander et al. |
| 8,799,269 B2 | 8/2014 | Friedlander et al. |
| 8,903,813 B2 | 12/2014 | Friedlander et al. |
| 8,931,109 B2 | 1/2015 | Adams et al. |
| 8,983,981 B2 | 3/2015 | Adams et al. |
| 9,053,102 B2 | 6/2015 | Adams et al. |
| 2008/0015913 A1 | 1/2008 | Courtney et al. |
| 2009/0024553 A1* | 1/2009 | Angell .................. G06N 5/025 706/47 |
| 2011/0071975 A1* | 3/2011 | Friedlander ......... G06F 17/3051 706/47 |
| 2011/0270768 A1 | 11/2011 | Alvarez et al. |
| 2012/0095775 A1 | 4/2012 | Burton et al. |
| 2013/0254202 A1 | 9/2013 | Friedlander et al. |
| 2014/0067813 A1 | 3/2014 | Friedlander et al. |
| 2014/0074885 A1 | 3/2014 | Adams et al. |
| 2014/0358952 A1 | 12/2014 | Adams et al. |
| 2014/0373182 A1 | 12/2014 | Peri et al. |
| 2015/0227516 A1 | 8/2015 | Adams et al. |
| 2015/0234900 A1 | 8/2015 | Adams et al. |

\* cited by examiner

PROBABILISTIC INFERENCE ENGINE BASED ON SYNTHETIC EVENTS FROM MEASURED DATA

BACKGROUND

The invention relates generally to predicting a cognitive state of a user, and more particularly to building synthetic events from measured data sources, such as sensors, and processing these synthetic events to denote a probabilistic inference.

The amount of measure data is growing at an exponential rate. Many times this results in too much data and too many kinds of data. The data is often unlabeled and uncatalogued. Moreover, in entities with different levels, such as a corporation, there may specific rules or procedures for each level, e.g. department rules, functional area rules, division rules, and corporate wide rules. Many times every level of every entity has rules applicable to their data. Rules are often conflict one with another. The application of rules to data become combinatoric explosive.

The is currently no efficient and effective to go from sets of data and at various levels and combine them into labelled, repeatable and definable events. Next take those events and convert them into a probabilistic inference.

SUMMARY

Disclosed is a computer program product, system and computer-implemented method to map synthetic events, such as subject blink rate, subject respiration rate, room temperature, ambient noise level, etc., to probabilistic inference. In other words, the inventors have discovered away to automatically create abstractions of large sets of data and then reasons or inferences based on the abstractions.

In one example, the present invention understands the data by the data type and the data source. A logical hierarchy of a set of a plurality of synthetic events related by characteristics of the data. The logical hierarchy describes the shared characteristics of the data grouped similarly to what a smart human analyst would produce. The use of synthetic events reduces both the volume and dimensionality of the data. A probabilistic event based upon the characteristic of the data is derived from the logical hierarchy of a set of plurality of synthetic events using Bayesian statistics. This provides easy classification rules and identifies overlaps or conflicts of the data's metadata characteristics.

In one example, the computer program product, system and computer-implemented method generates a probabilistic inference based on generating synthetic events. The probabilistic inference is derived from the logical hierarchy using Bayesian statistics to infer a probabilistic event based upon a characteristic of the data in a hierarchy of synthetic events. The logical hierarchy of a set of a plurality of synthetic events is related by at least one characteristic of data is built by accessing a first set of data. The first set of data is organized based on a first characteristic. A second set of data different than the first set of data is accessed. A second set of data based is organized based on a second characteristic. The first characteristic and the second characteristic are processed to generate a synthetic event. The synthetic event is a third set of data representing a result of a mathematical computation defined by an operation $S(p1) \Longrightarrow F(p2)$. S is a set of input facts with probability p1. The set of input facts is the first characteristic and the second characteristic. F is an inferred event with probability p2.

The term "event" means a particular set of data that represents, encodes, or records at least one of a thing or happening. Each of the first set of data, the second set of data, the first characteristic, the second characteristic, and the synthetic event all are different events.

The details of the preferred embodiments of the invention, both as to its structure and operation, are described below in the Detailed Description section in reference to the accompanying drawings. The Summary is intended to identify key features of the claimed subject matter, but it is not intended to be used to limit the scope of the claimed subject matter.

BRIEF DESCRIPTION OF THE DRAWINGS

The accompanying figures wherein reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

Figure 1:
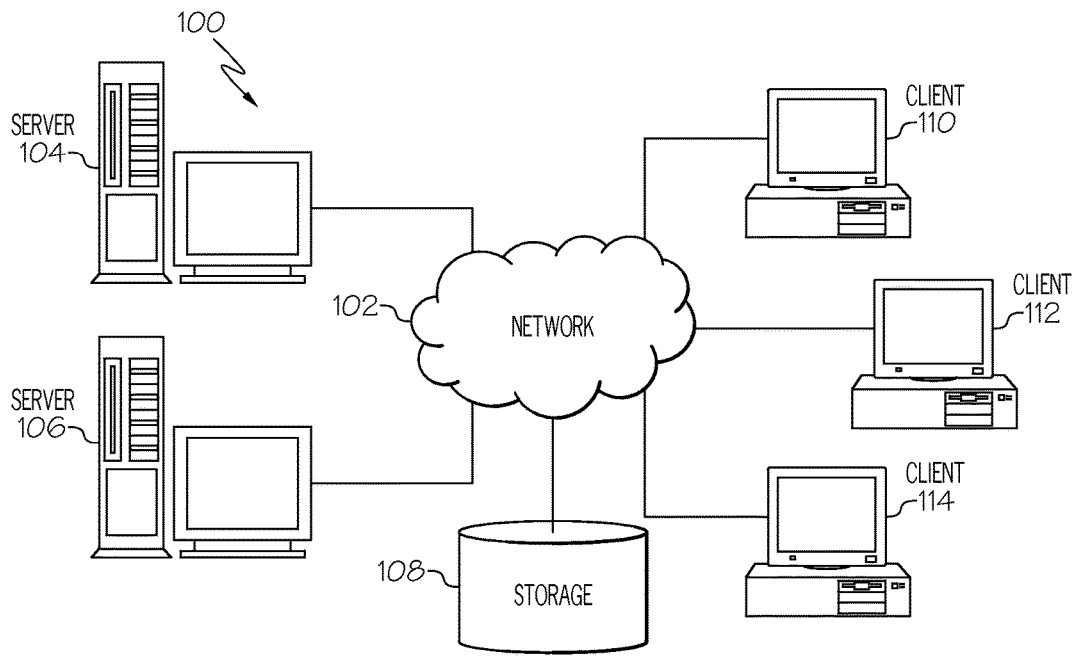
FIG. 1 is a pictorial representation of a data processing system in which an illustrative embodiment may be implemented.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

One aspect of the invention is to map synthetic events, such as subject blink rate, subject respiration rate, room temperature, ambient noise level, etc., to probabilistic inference. In other words, the inventors have discovered away to create abstractions automatically of large sets of data and then reasons or inferences based on the abstractions. The present invention reduces both the volume of data and the dimensionality of applicable rules by using synthetic events. Rules packages are probabilistically associated with a common reference information hierarchy (conformed dimensions). The conformed dimensions are shared reference information across multiple data sources. (Dates hierarchies are the same everywhere). This provides easy classification of the rules—both for human and machine usage. The synthetic event analysis will support identifying overlaps or conflicts of rules. The rules may include specific instructions related to physical separation, security, and labeling.

Non-Limiting Definitions

The terms "a", "an" and "the" are intended to include the plural forms as well, unless the context clearly indicates otherwise.

The terms "comprises" and/or "comprising", when used in this specification, specify the presence of stated features, steps, operations, elements, and/or components, but do not preclude the presence or addition of one or more other features, integers, steps, operations, elements, components, and/or groups thereof.

The phase "characteristic of data", means an attribute or quality relating the data. Example of the phrase characteristics of data include the physical source of data, the stated organizational source of data, the referenced organizational tagging, the stated classification, the date of ingestion of the data, the method of delivery of the data, geo tagging or location from which the data is accessed, the concurrency of data, or a combination thereof.

The term "conformed dimension" is a set of data attributes that have been physically referenced in multiple database tables using the same key value to refer to the same structure, attributes, domain values, definitions and concepts. A conformed dimension cuts across many facts. Dimensions are conformed when they are either exactly the same (including keys) or one is a perfect subset of the other. Most important, the row headers produced in two different answer sets from the same conformed dimension(s) must be able to match perfectly. Conformed dimensions are either identical or strict mathematical subsets of the most granular, detailed dimension. Dimension tables are not conformed if the attributes are labeled differently or contain different values. Conformed dimensions come in several different flavors. At the most basic level, conformed dimensions mean exactly the same thing with every possible fact table to which they are joined. The date dimension table connected to the sales facts is identical to the date dimension connected to the inventory facts.

The term "inferred artifact" is used to mean state of mind, mental focus, state of awareness, may reflect a physical need or desire. This artifact may or may not be directly mappable to the "real world".

The term "probabilistic inference" is an artificial probabilistic construct of an inferred artifact.

The term "synthetic event" and "synthetic cognitive event states" are artificial constructs used to model and process real world stimulus, states, and actions. They may or may not be directly mappable to real world events. Synthetic events and synthetic cognitive event states are probabilistic constructs with probabilities of −1.0 to 1.0. The synthetic event is an additive or non-additive aggregate. It is identified, identifiable, and categorized as one or several values reflecting the reduction of the dimensionality of the data according to an algorithm, formula or other process. The synthetic event may aggregate events or quantities of real or derivative values. It may be constructed of events or quantities of different cardinalities, units of measure, units of time. Further, synthetic events may aggregate multiple differently levels of event or quantity aggregation. In one example the synthetic event may be the product of a purposely specified and constructed algorithms or formulas or other processes or it may record "found values" from data mining or statistical techniques (including formulation).

Data Processing System

With reference now to the figures, FIG. 1 depicts a pictorial representation of a network of data processing systems in which an illustrative example may be implemented. Network data processing system 100 is a network of computers in which embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. These clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

In the depicted example, network data processing system 100 is the Internet with network 102 representing a world-wide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for different embodiments.

Figure 2:
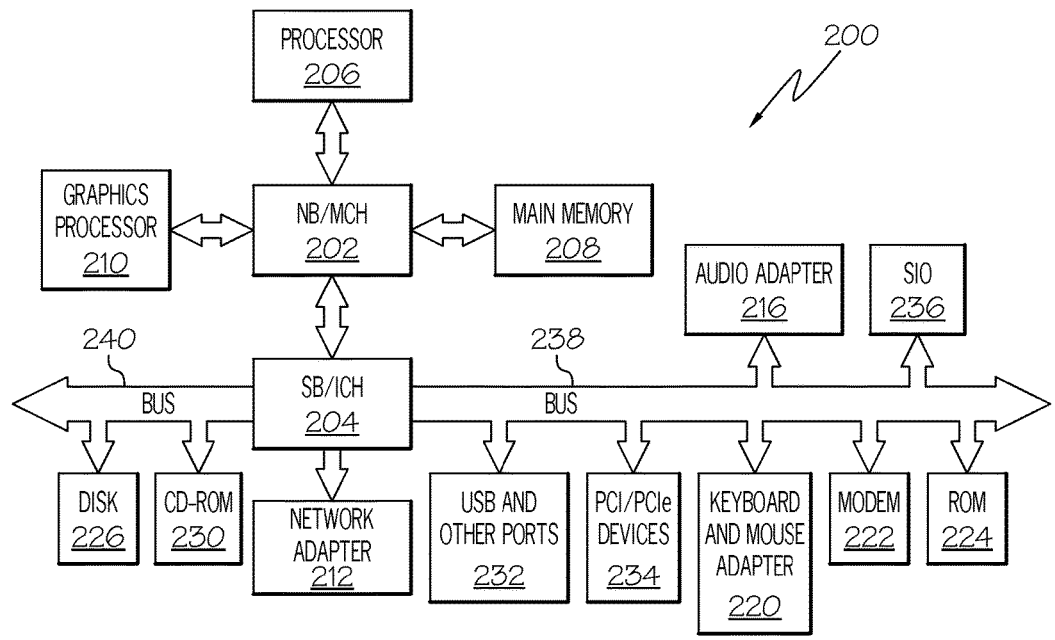
FIG. 2 is a block diagram of a data processing system in which an illustrative embodiment may be implemented.

With reference now to FIG. 2, a block diagram of a data processing system is shown in which an illustrative embodiment may be implemented. Data processing system 200 is an example of a computer, such as server 104 or client 110 in FIG. 1, in which computer usable code or instructions implementing the processes may be located for the different embodiments.

In the depicted example, data processing system 200 employs a hub architecture including a north bridge and memory controller hub (MCH) 202 and a south bridge and input/output (I/O) controller hub (ICH) 204. Processor 206, main memory 208, and graphics processor 210 are coupled to north bridge and memory controller hub 202. Graphics processor 210 may be coupled to the MCH through an accelerated graphics port (AGP), for example.

In the depicted example, local area network (LAN) adapter 212 is coupled to south bridge and I/O controller hub 204 and audio adapter 216, keyboard and mouse adapter 230, modem 232, read only memory (ROM) 234, universal serial bus (USB) ports and other communications ports 242, and PCI/PCIe devices 244 are coupled to south bridge and I/O controller hub 204 through bus 248, and hard disk drive (HDD) 236 and CD-ROM drive 240 are coupled to south bridge and I/O controller hub 204 through bus 240. PCI/PCIe devices may include, for example, Ethernet adapters, add-in cards, and PC cards for notebook computers. PCI uses a card bus controller, while PCIe does not. ROM 234 may be, for example, a flash binary input/output system (BIOS). Hard disk drive 236 and CD-ROM drive 240 may use, for example, an integrated drive electronics (IDE) or serial advanced technology attachment (SATA) interface. A super I/O (SIO) device 246 may be coupled to south bridge and I/O controller hub 204.

An operating system runs on processor 206 and coordinates and provides control of various components within data processing system 200 in FIG. 2. The operating system may be a commercially available operating system such as Microsoft Windows. An object oriented programming system, such as the Java programming system, may run in conjunction with the operating system and provides calls to the operating system from Java programs or applications executing on data processing system 200.

Instructions for the operating system, the object-oriented programming system, and applications or programs are located on storage devices, such as hard disk drive 236, and may be loaded into main memory 208 for execution by processor 206. The processes of the illustrative embodiments may be performed by processor 206 using computer implemented instructions, which may be located in a memory such as, for example, main memory 208, read only memory 234, or in one or more peripheral devices.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. Also, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may be comprised of one or more buses, such as a system bus, an I/O bus and a PCI bus. Of course the bus system may be implemented using any type of communications fabric or architecture that provides for a transfer of data between different components or devices attached to the fabric or architecture. A communications unit may include one or more devices used to transmit and receive data, such as a modem or a network adapter. A memory may be, for example, main memory 208 or a cache such as found in north bridge and memory controller hub 202. A processing unit may include one or more processors or CPUs. The depicted examples in FIGS. 1-2 and above-described examples are not meant to imply architectural limitations. For example, data processing system 200 also may be a tablet computer, laptop computer, or telephone device in addition to taking the form of a PDA.

Synthetic Event

Figure 3:
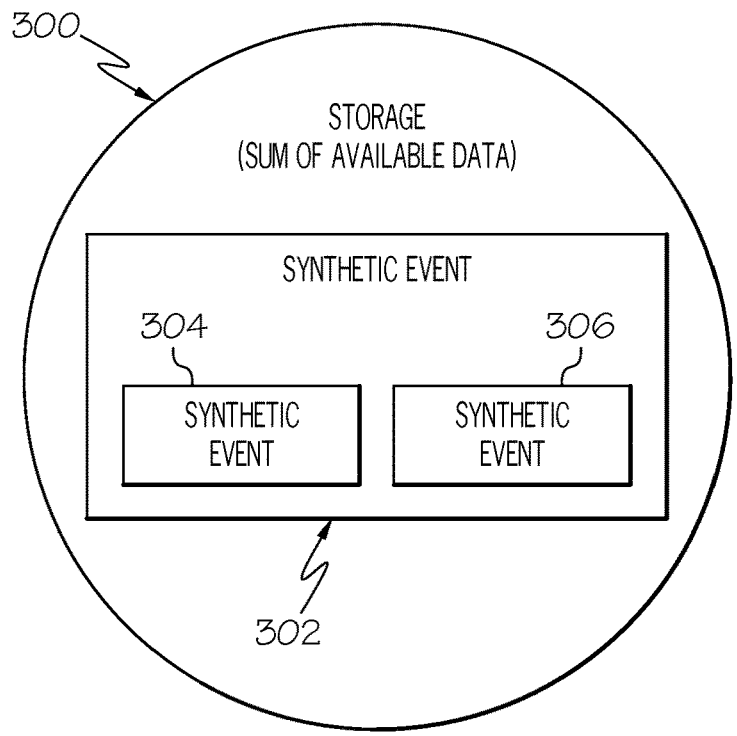
FIG. 3 is a block diagram illustrating a combination of synthetic events, in accordance with an illustrative embodiment.

FIG. 3 is a block diagram illustrating a combination of synthetic events, in accordance with an illustrative embodiment. Storage 300 represents the storage devices that contain the sum of available data. The techniques described for creating synthetic events are described in U.S. Pat. No. 8,145,582, entitled "Synthetic Events for Real Time Patient Analysis" the teaching of which is hereby incorporated by reference in its entirety.

The process shown in FIG. 3 can be implemented using one or more data processing systems, including but not limited to computing grids, server computers, client computers, network data processing system 100 in FIG. 1, and one or more data processing systems, such as data processing system 200 shown in FIG. 2. Together, devices and software for implementing the process shown in FIG. 3 can be referred-to as a system.

The term datum is defined as a single fact represented in a mathematical manner, usually as a binary number. A datum could be one or more bytes. Events can be processed by computers by processing objects that represent the events. An event object is a set of data arranged into a data structure, such as a vector, row, cube, or some other data structure. A given activity may be represented by more than one event object. Each event object might record different attributes of the activity. Non-limiting examples of events include purchase orders, email confirmation of an airline reservation, a stock tick message that reports a stock trade, a message that reports an RFID sensor reading, a medical insurance claim, a healthcare record of a patient, a video recording of a crime, and many, many other examples.

An example of an analysis is the generation of generate synthetic event 304 according to the formula $S(p1) \Longrightarrow F(p2)$. As more synthetic events are generated, user feedback provided, and as additional raw data become available, the analysis process can be iterated many times until a reliable and accurate answer is achieved. As a result, a truly vast amount of data can be analyzed to find conclusions and reasons for why the conclusions are true or false. The conclusions can be extremely specific, even down to the individual person or user.

FIG. 3 shows that synthetic events can be generated individually or by combining other synthetic events. Thus, based on storage 300, synthetic event 302 can be generated by combining and/or analyzing synthetic event 304 and synthetic event 306. The resulting synthetic event 302 is reported and then stored for future analysis.

Figure 4:
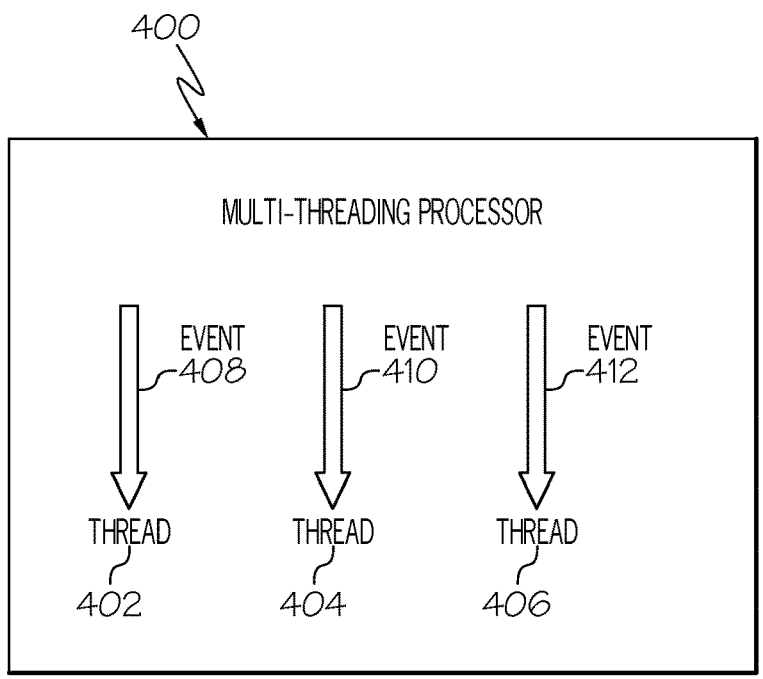
FIG. 4 is a block diagram illustrating processing of events in a processor having multi-threading processing capability, in accordance with an illustrative embodiment.

FIG. 4 is a block diagram illustrating processing of events in a processor having multi-threading processing capability, in accordance with an illustrative embodiment. Processor 400 can be processor 200 shown in FIG. 2, or can be one or more processors acting together to provide multi-threading functionality. Multi-threading functionality is often provided by parallel-processing processors.

Processor 400 can be used to more quickly perform synthetic event analysis, as described with respect to FIG. 3. Specifically, each thread, thread 402, thread 404, and thread 406 processes a corresponding distinct event. Thus, thread 402 processes event 408, thread 404 processes event 410, and thread 406 processes event 412. Because each event is processed by a different thread, the entire process of performing analysis is increased. Further, as events are combined into broader events, the number of threads operating can be decreased. Still further, two or more threads could process different aspects of a single event, thereby further increasing the speed of processing.

A synthetic event is defined above is as an even that represents a probability of a future fact or happening, or that represents a probability that a potential past fact or happening has occurred, or that represents a probability that a potential current fact or happening is occurring, with the mathematical formulation of a synthetic event represented by the operation $S(p1) \Longrightarrow F(p2)$, where S is the set of input facts with probability p1 that potentiates future event F with probability p2. Note that future event F in this operation can represent represents a probability that a potential past fact or happening has occurred, or that represents a probability that a potential current fact or happening is occurring, because these probabilities did not exist before a request to calculate them was formulated. Additionally, a synthetic event can be considered a recordable, definable, addressable data interrelationship in solution space, wherein the interrelationship is represented with a surrogate key, and wherein the synthetic event is able to interact with other events or facts for purposes of computer-assisted analysis.

Synthetic events are composed of physically or logically observable events, not suppositions about mental state, unless they can be supported by or characterized as observable fact or numbers. Synthetic events can be compared to generate additional synthetic evens. For example, a previously derived synthetic event is a conclusion that business "B" appears to be entering a market area with probability p1. A second previously derived synthetic event is that, within probability p2, an unknown company is engaging in a large scale hiring of personnel with skill necessary to compete with a particular product line. These two synthetic events can be compared and processed to derive a probability, p3, that business "B" intends to enter into business competition with the particular product line. Other events or synthetic events could be added or combined to the first two previous synthetic events to modify the probability p3.

Hierarchy of Synthetic Events

Figure 5:
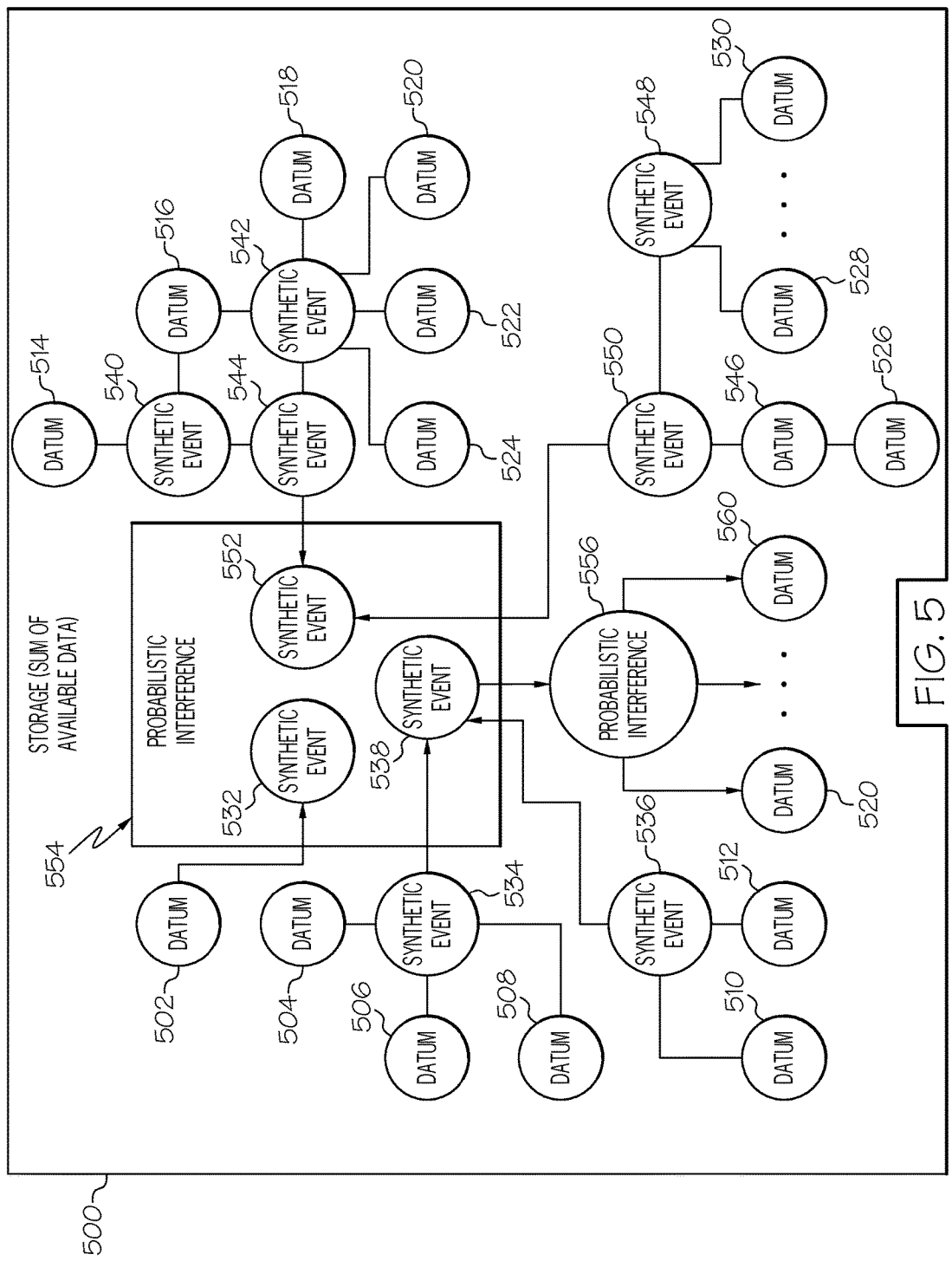
FIG. 5 is a block diagram illustrating combinations of synthetic events to derive an inference, in accordance with an illustrative embodiment.

FIG. 5 is a block diagram illustrating combinations of synthetic events to derive an inference, in accordance with an illustrative embodiment. Each synthetic event shown in FIG. 5 can be generated and stored according to the techniques described with respect to FIG. 3 through FIG. 4. Thus, the process shown in FIG. 4 can be implemented using one or more data processing systems, including but not limited to computing grids, server computers, client computers, network data processing system 100 in FIG. 1, and one or more data processing systems, such as data processing system 200 shown in FIG. 2.

Before describing combinations of synthetic events to derive an inference generate, several terms are defined. The term "datum" is a set of data defined as a single fact represented in a mathematical manner, usually as a binary number.

Events can be processed by computers by processing objects that represent the events. An event object is a set of data arranged into a data structure, such as a vector, row, cube, or some other data structure. A given activity may be represented by more than one event object. Each event object might record different attributes of the activity. Non-limiting examples of "events" include purchase orders, email confirmation of an airline reservation, a stock tick message that reports a stock trade, a message that reports an RFID sensor reading, a medical insurance claim, a healthcare record of a patient, a video recording of a crime, and many, many other examples.

A complex event is defined as an abstraction of other events which are members of the complex event. A complex event can be a synthetic event, though a synthetic event need not be a complex event. Examples of complex events include the 1929 stock market crash (an abstraction denoting many thousands of member events, including individual stock trades), a CPU instruction (an abstraction of register transfer level events), a completed stock purchase (an abstraction of the events in a transaction to purchase the stock), a successful on-line shopping cart checkout (an abstraction of shopping cart events on an on-line website), and a school transcript (an abstraction of a record of classes taken by a particular student). Many, many other examples of complex events exist.

A synthetic event can be considered a recordable, definable, addressable data interrelationship in solution space, wherein the interrelationship is represented with a surrogate key, and wherein the synthetic event is able to interact with other events or facts for purposes of computer-assisted analysis.

Synthetic events are composed of physically or logically observable events, not suppositions about mental state, unless they can be supported by or characterized as observable fact or numbers. Synthetic events can be compared to generate additional synthetic events. For example, a previously derived synthetic event is a conclusion that business "B" appears to be entering a market area with probability p1. A second previously derived synthetic event is that, within probability p2, an unknown company is engaging in a large scale hiring of personnel with skill necessary to compete with a particular product line. These two synthetic events can be compared and processed to derive a probability, p3, that business "B" intends to enter into business competition with the particular product line. Other events or synthetic events could be added or combined to the first two previous synthetic events to modify the probability p3.

Returning to FIG. 5, the improved genesis of synthetic events is described. Storage 500 represents one or more storage units, including RAM, ROM, hard drives, flash disks, or any other form of memory. Storage 500 contains the sum of data available for processing. As described above, data is preferably stored at the atomic level, meaning that each individual datum is addressable and recordable and has associated with it metadata that allows meaningful manipulation of the data. Any given amount of data can exist within storage 500, though in this example storage 500 includes datum 502, datum 504, datum 506, datum 508, datum 510, datum 512, datum 514, datum 516, datum 518, datum 520, datum 522, datum 524, datum 526, datum 528, and datum 530, which are all present before the creation of a synthetic event.

A logical hierarchy of the set of plurality of synthetic events, can group these synthetic events based on a characteristic of data. The logical hierarchy can comprise two or more synthetic events, such as for example in the case of probabilistic inference 554, which includes datum 502, synthetic event 532 is different from datum 502 in that synthetic event 532 includes additional data that makes it a potential grouping if at least one additional datum is included in synthetic event 532.

As implied above, multiple datums (data) can be represented as a single synthetic event. Thus, for example, datum 504, datum 506, and datum 508 together are part of synthetic event 534. Likewise, datum 510 and 512 together are part of synthetic event 536. Similarly, datum 514 and datum 516 together are part of synthetic event 540; and datum 518, datum 520, datum 522, and datum 524 together are part of synthetic event 542. A synthetic event, such as synthetic event 548 can include a vast plurality of data, as represented by the ellipsis between datum 528 and datum 530. Finally, datum 526 is part of synthetic event 546.

To add additional levels of abstraction, each level of the logical hierarchy of a set of a plurality of synthetic events can themselves be combined into broader the logical hierarchy of a set of a plurality of synthetic events. For example, synthetic event 534 is combined with synthetic event 536 to the logical hierarchy of a set of a plurality of synthetic events 538.

Many levels of synthetic events and abstraction are possible into the logical hierarchy of a set of a plurality of synthetic events. For example, synthetic event 540 and synthetic event 542 combine to form the logical hierarchy of a set of a plurality of synthetic events 544. Synthetic event 546 and synthetic event 548 combine to form the logical hierarchy of a set of a plurality of synthetic events t 550. Thereafter, the logical hierarchy of a set of a plurality of synthetic events 544 and the logical hierarchy of a set of a plurality of synthetic events 550 are themselves combined to form the logical hierarchy of a set of a plurality of synthetic events 552.

Each level of the logical hierarchy of a set of a plurality of synthetic events synthetic event can be processed as a single pointer, even synthetic events having billions, trillions, or more members can be processed as a single pointer. For this reason, computationally explosive computations become manageable.

In the illustrative embodiment of FIG. 5, the logical hierarchy of a set of a plurality of synthetic events 532, 538, and 552 are to be analyzed to infer at least one probabilistic event 554. An example of an analysis is inference analysis, is using Bayesian statistics. An example of an analysis is the to infer at least one probabilistic event 554 according to the formula $S(p1) \Longrightarrow F(p2)$, as further described above.

As a result to infer at least one probabilistic event 554, the inferred the probabilistic event synthetic event 556 is formed. To infer the probabilistic event 554 could be composed of multiple synthetic events, of which to infer the probabilistic event 556 is a member. Thus, infer the probabilistic event 556 is a result of the analysis performed on the group comprising synthetic events 532, 538, and 552 in the logical hierarchy of synthetic events.

The infer the probabilistic event 556 itself is a pointer that refers to sub-members or sub-components related to the analysis. The sub-members or levels of hierarchy of infer the probabilistic event 556 are derived from the members of the level of hierarchy 532, 538, and 552. Thus, infer the probabilistic event 556 can be conceivably composed of a vast plurality of sub-members or levels of hierarchy. In this case, infer the probabilistic event 556 includes datum 558 through datum 560, together with many data represented by the ellipsis. Preferably, not all of the sub-members of a group synthetic events 532, 538, and 552 in the logical hierarchy of synthetic events are also sub-members of infer the probabilistic event 556. Part of the effort of the analysis that generates generate infer the probabilistic event 554 is to narrow the realm of relevant data in order to render computationally explosive calculations amenable to numerical solutions.

Additionally, infer the probabilistic event 556 can itself be a pointer that points to other infer the probabilistic events. Thus, for example, infer the probabilistic event 556 could have a pointer structure similar to the pointer structure that forms synthetic event 552.

Because each event or synthetic event or level of hierarchy to infer the probabilistic event is represented as a pointer, extremely specific information can be obtained. For example, infer the synthetic event 532 represents a genetic sequence of a particular patient, infer the synthetic event 538 represents a pool of genetic sequences, and infer the synthetic event 552 represents diet habits of a particular ethnic group. An inference analysis is performed with the goal of determining a probability that the particular patient will develop a form of cancer in his or her lifetime. In this illustrative embodiment, infer the probabilistic event 556 could be the group of individuals that are likely to develop cancer, with datum 558 representing the individual patient in question. Thus, a doctor, researcher, or analyst can "drill down" to achieve reliable conclusions regarding specific items or individuals based on an analysis of a truly vast body of data.

Overall Flow

Figure 6:
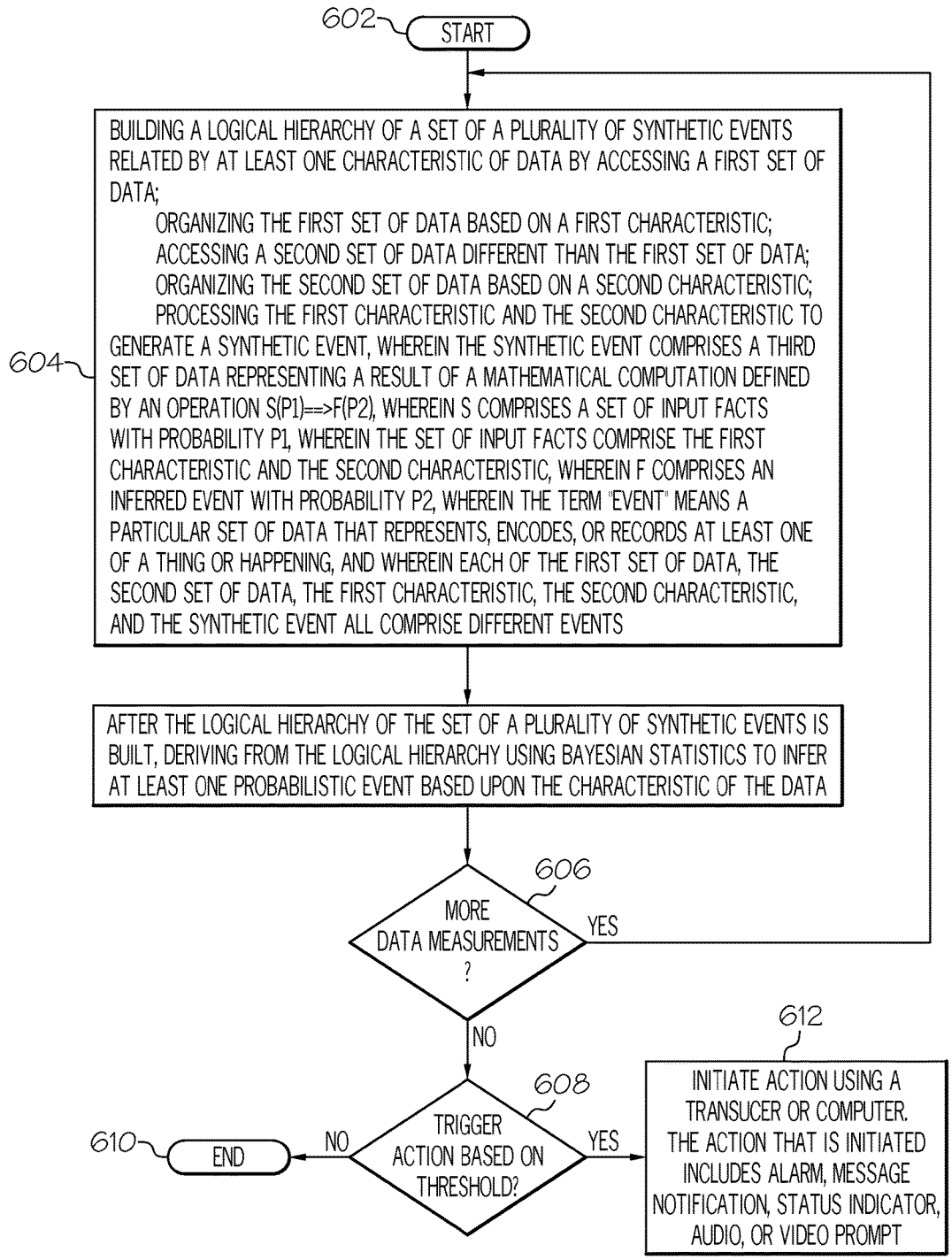
FIG. 6 is a flowchart of a process for deriving an inference from a logical hierarchy of synthetic events, in accordance with an illustrative embodiment.

FIG. 6 is a flowchart of a process for generating synthetic events, in accordance with an illustrative embodiment. The process shown in FIG. 5 represents a process performed to calculate a synthetic event, such as the synthetic events shown in FIG. 3.

The process begins in step 502 and immediately proceeds to step 504 in which the system accesses a set of data measurement from one or more physical sensors related to a user. In step 506, the system processes the data measurements to generate one or more synthetic events. Each of the synthetic events comprise a second set of data representing a result of a mathematical computation defined by an operation $S(p1) \Longrightarrow F(p2)$, wherein S comprises the first set of data measurements with probability p1. The F comprises an inferred event with probability p2, wherein each of the synthetic events is a particular set of data that represents, encodes, or records at least one of a thing or happening.

Next in step 508, the synthetic events in step 504, are processed to denote one or more synthetic emotional cognitive states of a user has been reached. Each of the synthetic emotional cognitive states comprise a third set of data representing a result of a mathematical computation defined by an operation $S'(p1') \Longrightarrow F'(p2')$, wherein S' comprises the second set of the one or more synthetic events with probability p1'. The F' comprises an inferred event with probability p2', wherein each of the first set of data, the synthetic events, and the synthetic emotional cognitive states all comprise different sets of data.

In step 510, a test is made to review if more data measurements are available for processing. If there is more data to process, the flow returns to step 504. Otherwise, in step 512 another test is made to see if the synthetic emotional cognitive state is above a settable threshold. In the event it is not the process may terminate in step 514. Otherwise, in the case the threshold is reached, in step 516, an action is initiated using a transducer or computer. The action that is initiated includes an alarm, message notification, status indicator, audio or video prompt.

All steps of this process in FIG. 3 through FIG. 6 are probabilistic. Each relationship is assumed to be a many to many Unless otherwise stated each all relationships are not mutually exclusive Each stimulus may go into null to many synthetic events. Each synthetic event may be dispatched to null to many synthetic cognitive units. Each cognitive unit may be used to drive null to many actions based on rule sets.

Non-Limiting Examples

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The subject matter described above is provided by way of illustration only and should not be construed as limiting. Various modifications and substitutions of the described components and operations can be made by those skilled in the art without departing from the spirit and scope of the present invention defined in the following claims, the scope of which is to be accorded the broadest interpretation so as to encompass such modifications and equivalent structures. As will be appreciated by those skilled in the art, the systems, methods, and procedures described herein can be embodied in a programmable computer, computer executable software, or digital circuitry. The software can be stored on computer readable media or computer program product. For example, computer readable media can include a floppy disk, RAM, ROM, hard disk, removable media, flash memory, a "memory stick", optical media, magneto-optical media, CD-ROM, etc.

What is claimed is:

1. A computer-implemented method to compute a probabilistic inference comprising:
building a logical hierarchy of a set of a plurality of synthetic events related by at least one characteristic of data by
accessing a first set of data;
organizing the first set of data based on a first characteristic;
accessing a second set of data different than the first set of data;
organizing the second set of data based on a second characteristic;
processing the first characteristic and the second characteristic to generate a synthetic event, wherein the synthetic event comprises a third set of data representing a result of a mathematical computation defined by an operation $S(p1) \Longrightarrow F(p2)$, wherein S comprises a set of input facts with probability $p1$, wherein the set of input facts comprise the first characteristic and the second characteristic, wherein F comprises an inferred event with probability $p2$, wherein the term "event" means a particular set of data that represents, encodes, or records at least one of a thing or happening, and wherein each of the first set of data, the second set of data, the first characteristic, the second characteristic, and the synthetic event all comprise different events;
after the logical hierarchy of the set of a plurality of synthetic events is built, deriving from the logical hierarchy using Bayesian statistics to infer at least one probabilistic event based upon the characteristic of the data;
evaluating against a threshold that the at least one probabilistic event has been reached; and
based the threshold being reached, triggering a transducer to take a physical action.

2. The computer-implemented method of claim 1, wherein the characteristic includes at least one temporal attribute.

3. The computer-implemented method of claim 1, wherein the characteristic includes at least one geographic attribute.

4. The computer-implemented method of claim 1, wherein the one or more of the synthetic events are grouped into one or more categories with a sum of each of the synthetic events in a category equal to one.

5. The computer-implemented method of claim 1, wherein the one or more of the synthetic events are distinct events represented by separate processes.

6. The computer-implemented method of claim 1, wherein the one or more of the synthetic events occur within a given time period.

7. The computer-implemented method of claim 1, wherein the accessing the first set of data from one or more physical sensors related to at least one user are data measurements of the user's geographical location.

8. The computer-implemented method of claim 1, wherein the accessing the first set of data from one or more physical sensors related to at least one user are data measurements of the user's biomedical data.

9. A computer program product for computing a probabilistic inference, the product having a computer readable non-transitory storage medium comprising program code operable for:
building a logical hierarchy of a set of a plurality of synthetic events related by at least one characteristic of data by
accessing a first set of data;
organizing the first set of data based on a first characteristic;
accessing a second set of data different than the first set of data;
organizing the second set of data based on a second characteristic;
processing the first characteristic and the second characteristic to generate a synthetic event, wherein the synthetic event comprises a third set of data representing a result of a mathematical computation defined by an operation $S(p1) \Longrightarrow F(p2)$, wherein S comprises a set of input facts with probability $p1$, wherein the set of input facts comprise the first characteristic and the second characteristic, wherein F comprises an inferred event with probability $p2$, wherein the term "event" means a particular set of data that represents, encodes, or records at least one of a thing or happening, and wherein each of the first set of data, the second set of data, the first characteristic, the second characteristic, and the synthetic event all comprise different events;
after the logical hierarchy of the set of a plurality of synthetic events is built, deriving from the logical hierarchy using Bayesian statistics to infer at least one probabilistic event based upon the characteristic of the data;
evaluating against a threshold that the at least one probabilistic event has been reached; and
based the threshold being reached, triggering a transducer to take a physical action.

10. The computer program product of claim 9, wherein the characteristic includes at least one temporal attribute.

11. The computer program product of claim 9, wherein the characteristic includes at least one geographic attribute.

12. The computer program product of claim 9, wherein the one or more of the synthetic events are grouped into one or more categories with a sum of each of the synthetic events in a category equal to one.

13. The computer program product of claim 9, wherein the one or more of the synthetic events are distinct events represented by separate processes.

14. The computer program product of claim 9, wherein the one or more of the synthetic events occur within a given time period.

15. The computer program product of claim 9, wherein the accessing the first set of data from one or more physical sensors related to at least one user are data measurements of the user's geographical location.

16. The computer-implemented method of claim 9, wherein the accessing the first set of data from one or more physical sensors related to at least one user are data measurements of the user's biomedical data.

17. A data processing system comprising:
a bus;
a processor connected to the bus;
a memory connected to the bus, the memory storing instructions for carrying out a computer implemented method, wherein the processor is capable of carrying out the instructions of:
building a logical hierarchy of a set of a plurality of synthetic events related by at least one characteristic of data by
accessing a first set of data;
organizing the first set of data based on a first characteristic;
accessing a second set of data different than the first set of data;
organizing the second set of data based on a second characteristic;
processing the first characteristic and the second characteristic to generate a synthetic event, wherein the synthetic event comprises a third set of data representing a result of a mathematical computation defined by an operation $S(p1) \Longrightarrow F(p2)$, wherein S comprises a set of input facts with probability $p1$, wherein the set of input facts comprise the first characteristic and the second characteristic, wherein F comprises an inferred event with probability $p2$, wherein the term "event" means a particular set of data that represents, encodes, or records at least one of a thing or happening, and wherein each of the first set of data, the second set of data, the first characteristic, the second characteristic, and the synthetic event all comprise different events;
after the logical hierarchy of the set of a plurality of synthetic events is built, deriving from the logical hierarchy using Bayesian statistics to infer at least one probabilistic event based upon the characteristic of the data;
evaluating against a threshold that the at least one probabilistic event has been reached; and
based the threshold being reached, triggering a transducer to take a physical action.

18. The data processing system of claim 17, wherein the characteristic includes at least one temporal attribute.

* * * * *